United States Patent
Rimm et al.

(12) 
(10) Patent No.: US 6,197,523 B1
(45) Date of Patent: Mar. 6, 2001

(54) METHOD FOR THE DETECTION, IDENTIFICATION, ENUMERATION AND CONFIRMATION OF CIRCULATING CANCER AND/OR HEMATOLOGIC PROGENITOR CELLS IN WHOLE BLOOD

(75) Inventors: David L. Rimm, Branford, CT (US); Robert A. Levine, 31 Pilgrim La., Guilford, CT (US) 06437; Stephen C. Wardlaw, Highrock, Lyme; Paul Fiedler, New Haven, both of CT (US)

(73) Assignee: Robert A. Levine, Guilford ( * ) Notice: Subject to any disclaimer, the term of this patent is extended or adjusted under 35 U.S.C. 154(b) by 0 days.

(21) Appl. No.: 08/976,886

(22) Filed: Nov. 24, 1997

(51) Int. Cl.[7] .................................................. G01N 33/574
(52) U.S. Cl. ............................ 435/7.1; 356/36; 435/7.22; 435/7.23; 435/7.24; 436/63; 436/64; 436/523; 436/813
(58) Field of Search .................................. 435/7.22, 7.23, 435/7.24, 7.1; 436/523, 63, 64; 356/36

(56) References Cited

U.S. PATENT DOCUMENTS

| | | | |
|---|---|---|---|
| 4,027,660 | * 6/1977 | Wardlaw et al. | 128/2 |
| 4,082,085 | * 4/1978 | Wardlaw et al. | 128/2 |
| 4,156,570 | * 5/1979 | Wardlaw | 356/36 |
| 5,086,784 | 2/1992 | Levine et al. | 128/771 |
| 5,198,927 | 3/1993 | Rathbone et al. | 359/385 |
| 5,251,474 | 10/1993 | Wardlaw et al. | 73/61.41 |
| 5,252,460 | 10/1993 | Fiedler et al. | 435/7.22 |
| 5,342,790 | 8/1994 | Levine et al. | 436/523 |
| 5,349,468 | 9/1994 | Rathbone et al. | 359/390 |
| 5,393,674 | 2/1995 | Levine et al. | 436/177 |
| 5,403,714 | 4/1995 | Levine et al. | 435/7.2 |
| 5,460,979 | 10/1995 | Levine et al. | 436/523 |
| 5,496,704 | 3/1996 | Fiedler et al. | 435/7.22 |
| 5,593,848 | 1/1997 | Levine et al. | 435/7.24 |
| 5,635,362 | 6/1997 | Levine et al. | 435/7.24 |
| 5,707,876 | 1/1998 | Levine | 436/177 |
| 5,834,217 | * 11/1998 | Levine et al. | 435/7.24 |

OTHER PUBLICATIONS

Webster's II New Riverside University Dictionary. p. 750, 1988.*

(List continued on next page.)

*Primary Examiner*—Christopher L. Chin
(74) *Attorney, Agent, or Firm*—William W. Jones

(57) ABSTRACT

A method for analyzing blood enables one to isolate, detect, enumerate and confirm under magnification the presence or absence of target cancer cells and/or hematologic progenitor cells which are known to circulate in blood. The analysis is performed in a sample of centrifuged anticoagulated whole blood. The analysis involves both morphometric and epitopic examination of the blood sample while the blood sample is disposed in a centrifuged blood sampling tube. The epitopic analysis of the presence or absence of cancer cells relies on the detection of epitopes which are known to present only on cancer cells; and the epitopic analysis of the presence or absence of hematologic progenitor cells relies on the detection of epitopes which are known to present only on hematologic progenitor cells. The targeted epitopes on the target cell types are epitopes which are also known to be absent on normal circulating blood cells; and the target cancer cell epitopes are epitopes which are known to be absent on target hematologic progenitor cells. Fluorophors with distinct emissions are coupled with antibodies which are directed against the targeted epitopes. The morphometric analysis is performed by staining the cells in the blood sample with an intracellular stain such as acridine orange which highlights the intracellular cell structure. Both the morphometric and epitopic analyses are preferably performed at or near the platelet layer of the expanded buffy coat in the centrifuged blood sample. The morphometric analysis and/or the epitopic analysis may be performed under magnification both visually and/or photometrically.

13 Claims, 7 Drawing Sheets

OTHER PUBLICATIONS

Rickman et al. "Rapid diagnosis fo malaira by acridine orange staining of centrifuged parasites" The Lancet. vol. i, pp. 68–71, 1989.*

Goldblatt et al; "Cancer Cells in Circulating Blood: A Critical Review"; *The Journal of Exfoliative Cytology*; pp. 25–33; (1965);.

Nagy; "A Study of Normal, Atypical and Neoplastic Cells in the White Cell Concentrate of the Periphal Blood"; *The Journal of Exfoliative Cytology*; pp. 61–67; (1965);.

Malmgren; "Problems in Techniques Used in Blood Specimen Preparation"; *The Journal of Exfoliative Cytology*; pp. 97–99; (1965);.

Watne; "The Isolation of Tumor Cells From the Blood: Approaches to Technique Comparisons"; *The Journal of Exfoliative Cytology*; pp. 123–133; (1965);.

Christopherson; "Cancer Cells in the Peripheral Blood: A Second Look"; *The Journal of Exfoliative Cytology*; pp. 169–174; (1965); and.

Moore et al; "Clinical Aspects of Cancer Cells in the Blood"; *The Journal of Exfoliative Cytology*; pp. 175–179; (1965).

* cited by examiner

METHOD FOR THE DETECTION, IDENTIFICATION, ENUMERATION AND CONFIRMATION OF CIRCULATING CANCER AND/OR HEMATOLOGIC PROGENITOR CELLS IN WHOLE BLOOD

TECHNICAL FIELD

This invention relates to a method and assembly for the detection, identification, enumeration and confirmation of circulating cancer and/or hematologic progenitor cells in an anticoagulated whole blood sample which is contained in a transparent sampling tube assembly. The detection, identification, enumeration and confirmation steps can all be performed in situ in the sampling tube assembly. More particularly, the method of this invention involves the centrifugal density-based separation of the contents of the blood sample in a manner which will ensure that any circulating cancer and/or hematologic progenitor cells in the blood sample are physically displaced by their density into a predetermined axial location in the blood sample and in the sampling tube assembly, and also into a restricted optical plane in the sampling tube assembly which is adjacent to the wall of the sampling tube, and finally into a very well-defined zone of that optical plane.

BACKGROUND ART

Cytology is the science and technology involved in the morphological characterization of mammalian cells. Cytology has clinical utility in both human and veterinary medicine. Cytology is most often used to diagnose the presence or absence of malignancy in exfoliated or harvested cells: a) that are shed into a body cavity such as the pleural space or peritoneum; b) that are shed into a body fluid that is excreted as, for example, sputum or urine; c) that are obtained by scraping or brushing a body surface, such as the uterine cervix, the uterine cavity, or bronchial mucosa; or d) that are obtained by direct needle-mediated aspiration from a tumor such as tumors of the thyroid, breast, lung, or the like. The exfoliated or harvested cells are then typically fixed, stained and visually studied, usually by bright field microscopy, and then, if needed, by immunologic stains and/or other molecular techniques.

This year approximately five hundred sixty thousand people will die from solid tumors (predominantly carcinomas) in the USA. Many of these deaths could be prevented by early diagnosis of these malignancies. Unfortunately, with the possible exception of the Prostate Specific Antigen (PSA) test for prostate cancer, there is no practical and routine methods that have been found to be effective for early detection of solid tumors through blood analysis.

Through early detection of cervical cancer, the Pap smear has decreased mortality from cervical cancer in the United States by over seventy percent. Development of an analogous test for other solid tumors could have a similar impact on overall cancer mortality.

The presence of circulating cancer cells that are spontaneously shed by cancerous tumors into the circulating blood stream which is supplying the tumors with oxygen and nutrients has been confirmed. The presence of such cells in the blood stream has been inferred for decades because of the spread of cancerous tumors by what has been described as the hematogenous route and on very rare occasions have been visualized in blood specimens. Recently sophisticated procedures which employ reverse transcriptase in conjunction with Polymerase Chain Reaction (PCR) have been able to detect the presence of tumor cells by their molecular signature in a significant number of patients with cancer, both when the cancer is localized and after it has spread.

An additional means of detecting circulating cancer cell employs a technology known as Fluorescent Activated Cell Sorting (FACS), such as that manufactured by Becton Dickinson and Company of Franklin Lakes, N.J. The FACS detection of circulating cancer cells involves detection of cancer cells by detecting fluorescent labeled antibodies which are directed against and bound to one or more epitopes that are present on or in cancer cells, and are not present on or in normal blood cells, and/or by detecting combinations of epitopes that are present on or in circulating normal blood cells and that may or may not be present on or in cancerous cells, or combinations of the aforesaid methods.

The FACS technology is thus based on cell highlighting, i.e., it is photometric and utilizes antibody-epitope specificity, and it cannot be used to morphologically analyze cells in situ in the FACS instrument. Both the reverse transcriptase/PCR, (the molecular method), and the FACS, (the immuno-phenotypic method), require that the origin of the tumor being sought be known in order to select for the specific molecular species or immuno-phenotypic signals. The aforesaid techniques have contributed to confirmation of the theory that cancer cells do circulate in the blood stream, but these techniques are not practical especially in point of care applications, by virtue of their cost and/or nature, for detecting the presence or absence of circulating tumorous cancer cells in the blood stream. Thus, there is no general or generic blood analyzing procedure for the detection and confirmation of the malignant nature of circulating cancer cells, regardless of their source, in a patient. In addition, neither the aforesaid molecular nor the immuno-phenotypic methods utilize in situ, i.e., in a closed sampling system, cytopathologically-based analyses to determine the morphometric characteristics of circulating cells which permit cancer cells to be identified and confirmed.

Since approximately eighty two percent of all cancers are epithelial in origin (seventy two percent of which are fatal), epithelial cancer cells should be detectable in circulating blood. While the presence of epithelial cells in the circulating blood stream does not, by itself, prove malignancy, it does alert the cytopathologist to the greater likelihood of malignancy since epithelial cells are not normally seen in the circulating blood stream. In certain cases, however; such as after surgery; or as a result of physical trauma; or as a result of dental flossing, or in cases of prostatitis, for example, it is possible that non-malignant epithelial cells may be found in the circulating blood stream. Visual morphological analysis of cells is currently the most reliable way to distinguish cancerous epithelial cells from benign epithelial cells which are found in the circulating blood sample. One problem which exists in connection with attempts to detect circulating cancer cells in blood via morphological analysis relates to the fact that circulating cancer cells in blood are often virtually indistinguishable from circulating hematologic progenitor cells, or blasts, by cytological analysis alone.

The paucity of cancer cells that may be present in a sample of circulating blood would require the cytopathologist to carefully examine approximately ten million nucleated blood cells in order to find one cancer cell, and that one cancer cell would be randomly located in the ten million nucleated blood cells, which in turn will themselves be homogeneously dispersed in a sea of five billion non-nucleated cellular blood constituents, i.e., the erythrocytes, plus two hundred fifty million platelets, all of which will be found in one milliliter of blood. Such a task would be very time consuming, and is thus impractical for use in analyzing a patient's blood for the presence or absence of cancer cells.

Another type of rare circulating nucleated cells which may be found in a blood sample are hematologic progenitor cells (HPC's), which include blasts, stem cells, and other progenitors of normally circulating cells are not usually present in a sample of circulating blood at levels which can be detected by the use of presently available hematotopic instruments, such as impedance counters and examination of stained peripheral blood. In patients who are receiving chemotherapy and in patients who are receiving human granulocyte colony-stimulating factor (HGCSF), and other similar cytokines, HPC's are more likely to be present, but generally at very low numbers, i.e., at about one to one thousand per ml, or less, of the sample. Thus, low concentrations of HPC's in a blood sample renders the HPC's non-detectable by routine methods.

It is important to detect and enumerate the HPC's because their enumeration can permit more efficient harvesting of the HPC's for clinically important stem cell transplant therapies. Similarly, the detection of circulating cancer cells in patients whose HPC's are being harvested is important so that reinfusion into the patient of harvested circulating cancer cells can be minimized.

A technique has been developed to measure constituent layers in a complex material mixture by centrifuging a sample of the material mixture in a capillary or other tube which contains an insert, typically a float. The float is preferably cylindrical, and has a specific gravity which causes it to settle into the centrifuged mixture to a degree which creates an annular free volume in the tube into which the layer, or layers to be measured will settle. The layers to be measured are thus physically elongated, and can thus be more easily and accurately measured. The aforesaid technique is described in U.S. Pat. Nos. 4,027,660, issued Jun. 7, 1977; 4,082,085 issued Apr. 4, 1978; 4,156,570 issued May 29, 1979; and others. This technology is presently being marketed by Becton Dickinson and Company under the registered trademark "QBC". This "QBC" technology has been adapted for use in the isolation and identification of microfilarial infestation of a blood sample, as set forth in U.S. Pat. No. 4,190,328, issued Feb. 26, 1980. U.S. Pat. Nos. 5,403,714, issued Apr. 4, 1995; 5,496,704, issued Mar. 5, 1996; 5,506,145, issued Apr. 9, 1996; and others describe the use of the aforesaid "QBC" technology to assay anticoagulated whole blood for various analytes; and also to assay tissue samples for the presence or absence of cancerous tumor cells, wherein tissue samples are admixed with a saline buffer solution prior to analysis.

It is evident that there exists a compelling need for a simple procedure and a system for performing such a procedure whereby a sample of capillary blood or venous blood could be quickly and accurately analyzed for the presence or absence of circulating cancer cells and/or hematologic progenitor cells. Additionally, the procedure should enable one to differentiate cancer cells from hematologic progenitor cells; and also enable one to confirm the nature of detected cells, all in situ, in the blood sampling paraphernalia.

DISCLOSURE OF THE INVENTION

This invention relates to a method and apparatus for visually or photometrically detecting circulating cancer and/or hematologic progenitor cells in an anticoagulated whole blood sample, which blood sample is contained in a transparent sampling tube. The detection and confirmation of circulating cancer and/or hematologic progenitor cells in the blood sample can be attained in a matter of minutes by utilizing the fact that circulating cancer cells which are of epithelial origin, and hematologic progenitor cells, when present in the circulating blood stream, have a different density than the other nucleated constituents of blood and, when gravimetrically separated, the epithelial cancer and/or hematologic progenitor cells will layer out in, or adjacent to, the platelet layer of the centrifuged blood sample. We have determined that circulating epithelial cancer and/or hematologic progenitor cells do not layer out by sedimentation, i.e., by size, in the centrifuged blood sample, but rather layer out by density in the centrifuged blood sample. The platelet layer is a blood constituent layer which is generally devoid of nucleated cells, and is also free of materials which are susceptible to DNA staining, thus allowing quick identification of nucleated cells which are in the vicinity of the platelet layer.

This invention allows in situ, i.e., in the sampling paraphernalia, visual morphometric analysis and also labeled epitopic analysis and identification of suspicious, i.e., large cells of low specific gravity, nucleated cells which are found in the centrifuged blood sample. The invention also can allow in situ analysis of the suspicious cells in the sampling tube assembly. Such analysis can confirm whether individual suspicious cells are epithelial and malignant; epithelial and benign; or non-epithelial in origin but are hematologic progenitor cells, all without removing the blood sample from the sampling tube. A significant advantage to using the "QBC" paraphernalia to isolate and identify circulating cancer and/or hematologic progenitor cells in anti-coagulated whole blood is that the "QBC" paraphernalia provides a closed system which is not susceptible to cross contamination from other samples. This advantage is very important in a reliable rare event detection system.

The cancer and/or hematologic progenitor cells in question are found to be in the vicinity of the platelet layer in a blood sample which has been centrifuged in the aforesaid "QBC" tube and insert paraphernalia, when the blood sample is examined under appropriate magnification. The procedure of this invention thus involves two steps which are each performed in situ while the blood sample remains in the sampling tube.

One step involves the detection of characteristic epitopic highlighting on the cells to determine the epithelial origin, or hematologic progenitor origin, of the nucleated cells noted in the tube. This step can be characterized as an "epitopic" analysis. In performing the epitopic step, one can use epithelial-specific antigens, such as E-cadherin, Cadherin 11, Epithelial membrane antigen (EMA), Carcino embryonic antigen (CEA), Integrins, EP-CAM, MUC3, CD-44, growth factor receptors, such as epidermal growth factor (EGF) receptor, Hepatocyte growth factor (HGF) receptor, among others for detection of cells of epithelial origin.

In order to detect cells of HPC origin, HPC epitopic-specific labeled antibodies which are directed against CD-33, CD34, for example, may be used. Epithelial cells will not be recognized by the aforesaid HPC-specific antibodies, nor will the HPC cells be recognized by the labeled epithelial-specific antibodies or other binding particles. Liposome encapsulation of the label may be used to enhance the ratio of signal to noise, and/or to change the density of the targeted cells. Encapsulation of dyes in liposomes, modification of the liposomes with binding agents, and attachment of labeled liposomes to target analytes in a sample, are all described in U.S. Pat. No. 5,593, 848, issued Jan. 14, 1997 to R. A. Levine et al, the contents of which patent are incorporated herein in their entirety.

The other step involves morphological examination of cells either to identify suspicious cells, or to confirm the malignant nature of the cells. The other step can therefore be characterized as a "morphometric" or "morphological;" analysis. A universal morphometric stain such as acridine orange, DAPI 4,6-diamidinone-2phenylindole, Hoechst, or "SYTO" brand dyes, or the like can be employed in this step. These two steps can be performed in either order, i.e., either one can be used to identify suspicious cells in the blood sample, and the other can be used to confirm the malignant or benign nature of any suspicious cells. The decision to rely on either the epitopic or morphometric analysis, or both, to determine the malignancy of a cell is dependent upon the type of tumor(s) that encountered. In some cases, the morphometric features alone are sufficiently characteristic so as not to require any additional confirmatory test. In other cases, an epitopic analysis may alone be sufficient. It is generally desirable and prudent to use both the epitopic and morphometric analyses in assaying the blood sample.

Morphometric analysis of suspicious nucleated cells that are detected in the vicinity of the platelet layer in the centrifuged blood sample can be accomplished by a cytopathologist visually, analyzing the blood sample either in situ in the tube, or by the cytopathologist visually analyzing an image, or a series of images, of the suspicious cells, which images are captured in situ in the tube, either manually by a technician-operated camera, or are captured automatically by an automated imaging instrument. The visual and image analysis or capture steps of the blood analysis method of this invention are all conducted with optical magnification of the centrifuged blood sample while the latter remains in the sampling tube. Morphometric analysis of captured images of nucleated cells from the blood sample can be remotely performed on the captured images.

Detection of nucleated cells which are suspected to be cancerous or of hematologic progenitor origin that are found in the centrifuged blood sample in the vicinity of the platelet layer can be based upon differential staining of the suspect cells as a result of the presence and/or absence of surface epitopes known to be present or absent on most epithelial cells, and/or on most epithelial cancer and/or hematologic progenitor cells, and are also known to be absent on normal circulating nucleated and nonnucleated blood cells or their precursors. Fluorophores or other detectable dyes or markers with distinctive emissions, such as Rhodamine, Fluorescein, Cy3, Cy5, Texas Red, Bodipy, or the like, can be coupled to antibodies or antigens, either directly, or after being encapsulated in liposomes as described in the aforesaid U.S. Pat. No. 5,593,848.

Another way to detect nucleated cells in the blood sample involves the addition to the blood sample of a universal nucleated cell stain such as acridine orange, Hoescht, DAPI, or "SYTO" brand dyes for example, which are capable of differentially staining all nucleated cells that may be found in the blood sample so as to differentially highlight and clarify the morphology of all of the nucleated cells in the blood sample.

The epitopic stains and the universal stain will maximally fluoresce at different wavelengths, thus allowing the detection of suspicious cells visually or by means of an automated instrument. For example, the centrifuged blood sample can be scanned by an appropriate instrument so as to identify all nucleated cells in the region of interest, and then scanned again with a different light filter set so as to identify all epithelial cells in the blood sample. In this way, cells can be identified which call for visual inspection for abnormal morphology. The visual morphometric examination can be performed as a preliminary detection test or it can be performed as the subsequent confirmatory test of the nature of the suspicious cells.

The preliminary morphometric visual analysis, or the photometric epitopic analysis, will be performed in the vicinity of the platelet layer of the expanded buffy coat in the blood sample. The fact that circulating cancer cells of epithelial origin, as exemplified by lung cancer, prostate cancer, breast cancer, rectal/colon cancer, ovarian cancer, and kidney cancer, among others, can be found in the vicinity of the platelet layer in a centrifuged sample of anticoagulated whole blood without the need of an extraneous density gradient, and can be morphologically and colorometrically identified in situ in the blood sample tube as being cancerous, is not described in the literature. Furthermore, the fact that circulating hematologic progenitor cells, which are derived from the bone marrow and are precursors of leukemia, can be found without the need of an extraneous density gradient in the vicinity of the platelet layer in a centrifuged sample of anticoagulated whole blood and can be epitopically identified, is likewise not described in the literature.

It is therefore an object of this invention to provide a method and apparatus for detecting, identifying and confirming the presence or absence of circulating cancer and/or hematologic progenitor cells in a centrifuged anticoagulated whole blood sample which is contained in a transparent tube.

It is an additional object of this invention to provide a method and apparatus of the character described wherein the circulating cancer and/or hematologic progenitor cells are isolated from a vast majority of non-cancerous and non-hematologic progenitor nucleated blood cells in the blood sample.

It is a further object of this invention to provide a method and apparatus of the character described wherein the preliminary detection step may be performed either visually or epitopically by appropriate instrumentation, and also wherein the subsequent confirmation step can be performed either visually or epitopically.

It is a supplementary object of this invention to provide a method and apparatus of the character described wherein isolated nucleated cells in the centrifuged blood sample can be confirmed as malignant or benign (negative), or as hematologic progenitor cells, in situ in the tube.

It is a further object of this invention to provide a method and apparatus of the character described which enables enumeration of detected circulating cancer and/or hematologic progenitor cells in the blood sample.

It is another object of this invention to provide a method and apparatus of the character described wherein the blood sample analysis is performed in situ in a closed system which system is resistant to contamination from ambient surroundings, thereby reducing the possibility of false positive results.

These and other objects and advantages of the invention will become more readily apparent from the following detailed description of the invention when taken in conjunction with the accompanying drawings, in which:

DETAILED DESCRIPTION OF THE INVENTION

Figure 1:
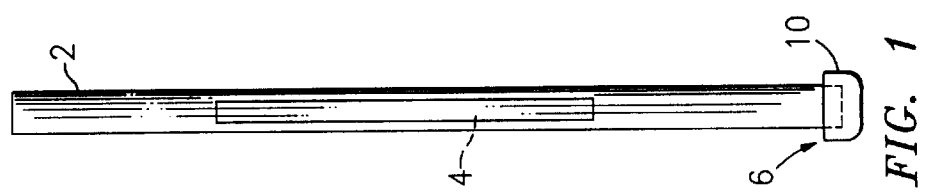
FIG. 1 is a side elevation view of a tube and float paraphernalia assembly which can be utilized to perform the procedure of this invention.

Referring now to the drawings, there is shown in FIG. 1 a side elevational view of a sampling tube and float assembly, which is referred to hereinafter generally as "the paraphernalia" and which includes a transparent sampling tube 2 which contains an elongated plastic insert or float 4. The tube 2 has a lower end 6 which is closed off by means of a closure cap 10. The tube 2 can be a capillary tube, or it can be a larger tube such as is described in U.S. Pat. No. 5,086,784, issued Feb. 11, 1992. The thickness of the gap between the tube bore and the insert 4 will be at least about ten microns so as to be accessible to target cells.

Figure 2:
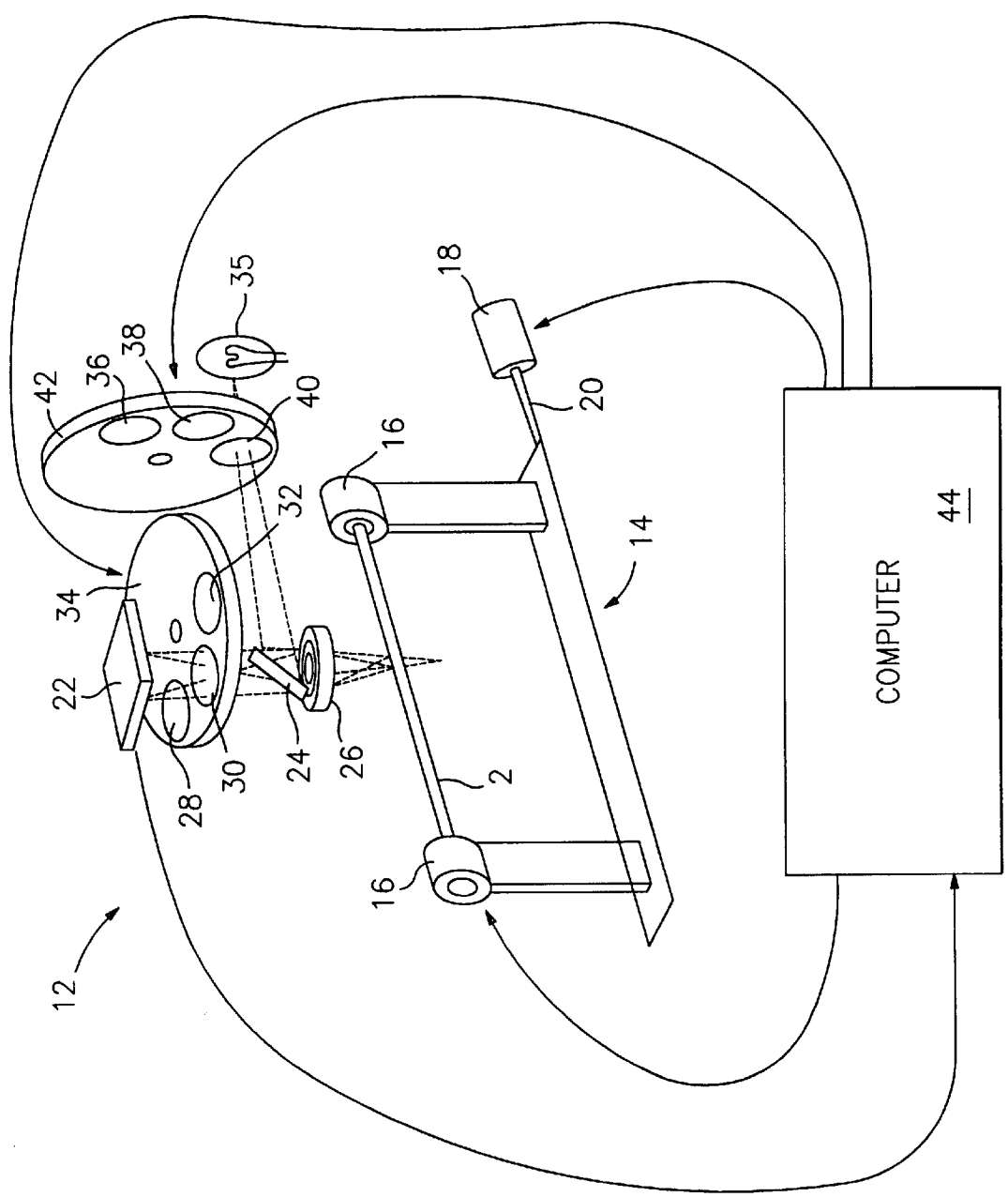
FIG. 2 is a schematic view of an automated microscopical instrument assembly which is adapted for use in conjunction with the paraphernalia of FIG. 1 to perform the procedure of this invention.

FIG. 2 is a schematic depiction of an automated calorimetric microscopical instrument assembly, which is denoted generally by the numeral 12, and which can be used to scan a centrifuged blood sample that is contained in the paraphernalia shown in FIG. 1, and can, without human intervention, colorometrically differentiate between different types of cells in the layers being scanned, and can create and store or transmit an image of the cell layers being scanned. The instrument assembly 12 includes a stage 14 which includes at least one rotatable support 16 which engages the ends of the sample tube 2 and enables the sample tube 2 to be rotated about its axis as the contents of the tube 2 are scanned. A reversible electric motor 18 selectively rotates a drive screw 20 in opposite directions so that the tube 2 can be axially moved in one direction and then in the reverse direction as the tube 2 is rotated stepwise in the stage 14. In this manner, the entire circumference contents of the tube 2 can be scanned. The automatic embodiment of the instrument assembly 12 includes a CCD camera 22 which, by means of a beam splitter 24 and lens 26, is focused upon the annular sample-containing gap in the tube assembly 2, which gap is located between the tube bore wall and the outer surface of the insert 4. It will be appreciated that the operating range of the lens 26 will be at least equal to the thickness of the gap between the tube bore and the insert 4 in the tube 2. The CCD camera 22 views and records images of the sample through a plurality of different emission light wave filters 28, 30 and 32 which are mounted on a selectively rotatable filter wheel 34. The instrument assembly 12 also includes an excitation light source 35 which directs an excitation light beam at the sample tube 2 through the beam splitter 24 and the focusing lens 26. A series of excitation light wave length filters 36, 38 and 40 are mounted on a selectively rotatable filter wheel 42. The excitation light beam is deflected by the beam splitter 24 toward the focusing lens 26, and is focused on the sample tube 2 by the lens 26. Thus, the two filter wheels 34 and 42 allow one to selectively control and vary the wave length of the excitation light source, as well as the emitted light source. A preprogrammed microprocessor controller 44 is operable to selectively control the rotation of the sample tube 2, the rotation of the filter wheels 34 and 42, and operation of the CCD camera 22. The controller 44 thus enables fully automatic operation of the instrument assembly 12 without the need of human intervention.

The instrument assembly 12 operates in the following manner to capture and record images of the results of scanning the blood sample contained in the tube 2 for suspicious nucleated cells, and also for confirming the malignant or benign nature of observed suspicious cells in situ in the blood sample. A venous or capillary sample of anticoagulated whole blood is drawn into the sampling tube 2 and insert 4 assembly. The blood sample will be admixed in the tube 2, or prior to being drawn into the tube 2, with a fluorescent morphological stain such as acridine orange, so that morphological characteristics of nucleated cells which are observed in the blood sample can be analyzed. The blood sample is also admixed with an epithelial cell-specific marker which is used to determine whether any suspicious cells noted in the blood sample are of epithelial origin. This confirmation procedure was chosen because all of the tumorous cancer cells which are being assayed are epithelial cells. A preferred antigen that is highly specific to a surface receptor on epithelial cells in E-cadherin. In order to tag any epithelial cells we prefer to use Cy3 conjugated directly to E-cadherin. The Cy3 is a marker that fluoresces at a different wavelength than acridine orange. The admixture of anticoagulated whole blood, acridine orange and E-cadherin/Cy3 is centrifuged for a time period of about five minutes in the sampling tube-insert assembly. The centrifuged sample is then placed in the supports 16 on the stage 14, and the instrument 12 is turned on. The CCD camera 22 will record images of the portion of the centrifuged blood sample as the latter is rotated and reciprocated back and forth through the focal plane of the camera 22. An image of the entire circumference of a target zone in the blood sample will thus be produced by the camera 22. Separate scans will be made, one of which will record the blood sample image as defined by an appropriate combination of the filters 28, 30, 32, 36, 38 and 40 which is selected so as to differentially fluoresce the acridine orange stain added to the sample. This scan will produce images of all nucleated cells in the zone of the blood sample being scanned. Another scan will record the blood sample image as defined by a second appropriate combination of the filters 28, 30, 32, 36, 38 and 40 which is selected so as to differentially fluoresce the E-cadherin, Cy3 or other label. This scan will produce images of all of the nucleated cells in the scanned zone of the blood sample which are epithelial cells.

Additional filter combinations can be used for additional scans depending on what additional cellular information is being sought. Such additional useful information could include additional cancer cell-specific epitopes which will enable the cytopathologist to identify the origin of the cancer cells, i.e., whether they are prostate cancer cells, breast cancer cells, lung cancer cells, ovarian cancer cells, or the like, which epitopic information is presently available, or becomes known in the future. The aforesaid analysis of the blood sample can be made automatically by the instrument shown in FIG. 2, or it can be performed by visually scanning the sample. The scanning steps and the analysis of the results of the scanning steps can be performed in either order. Scanning of the acridine orange-highlighted cells allows one to identify all of the nucleated cells in the scanned zone, and also allows one to analyze the morphology of the nucleated cells in order to identify any cells which appear to have a morphology which suggests malignancy. Scanning of the E-cadherin/Cy3 highlighted cells allows one to identify which of the nucleated cells in the scanned zone are epithelial cells. Confirmation of the presence of an epithelial cell (E-cadherin/Cy3-highlighted) having abnormal cell morphology (acridine orange-highlighted) in the centrifuged blood sample alerts the cytopathologist to the strong likelihood of a cancerous tumor in the blood sample donor. A similar protocol can be employed to determine whether suspicious nucleated cell are hematologic progenitor cells.

Referring now to FIGS. 3–14, there are depicted the results of photometric imaging of scans of blood samples taken with the "QBC" paraphernalia, and using the aforesaid technology.

We conducted experiments wherein cultured cancerous tumor cells were added to blood samples, to test both the limits of tumor cell detection, as well as to verify the differential morphology, and to determine the location of the tumor cells in the gravimetrically formed blood constituent density gradient. These experiments confirmed the veracity of the above-described procedure for isolating, analyzing and confirming the presence of circulating tumorous cancer cells in anticoagulated whole blood samples.

Figure 3:
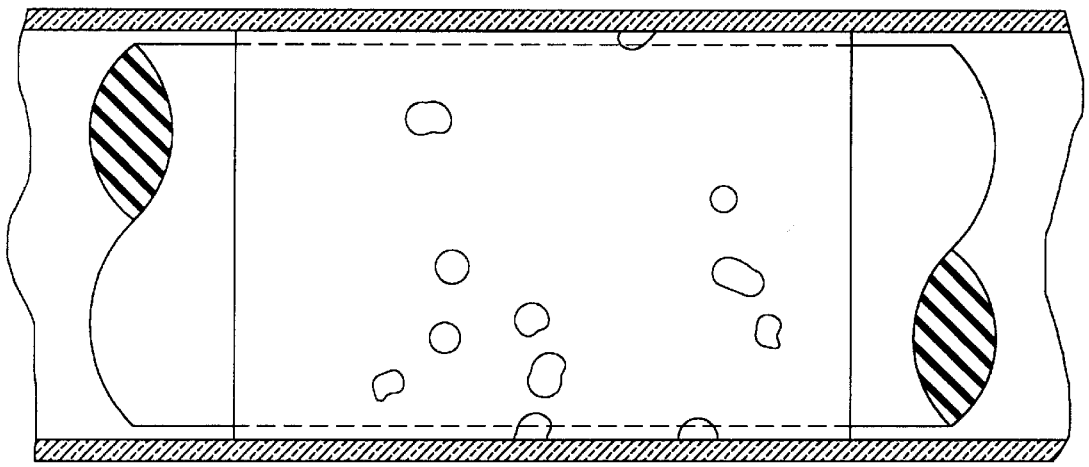
FIG. 3 is a graphic depiction of a photomicrograph taken of cultured breast cancer cells (MDA-MB-468) which were added to a sample of acridine orange-stained anticoagulated whole blood, and which cells were isolated, visually identified, and visually confirmed in the centrifuged blood sample using a 10x objective lens in an appropriately configured microscopical instrument assembly.
Figure 4:
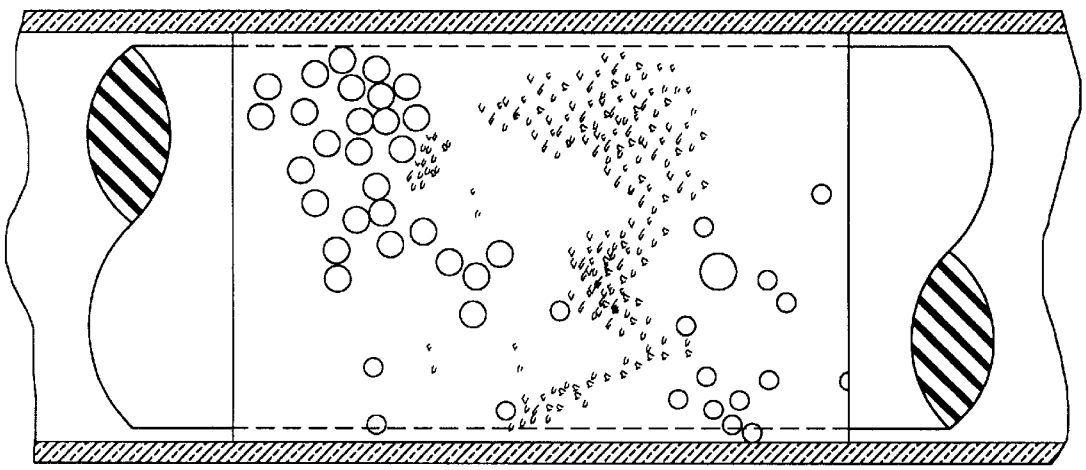
FIG. 4 is a graphic depiction of a photomicrograph taken of HT-29 colon cancer cells which were added to a sample of acridine orange-stained anticoagulated whole blood which cells were isolated, visually identified, and visually confirmed in situ in the tube containing the centrifuged blood sample using a 10x objective lens in an appropriately configured microscopical instrument assembly.

FIGS. 3 and 4 show recorded images of the morphologic appearance of an acridine orange-stained cultured breast cancer cell line, MDA-MB-468, (FIG. 3) and an acridine orange-stained cultured colon cancer cell line, HT-29, (FIG. 4) which cultured cancer cell lines were added to respective 100 $\mu$l samples of anticoagulated whole blood. The spiked blood samples were then analyzed in accordance with this invention. The blood sample analyses reliably and reproducibly identified the cultured breast and cultured colon cancer cells in the blood samples. The cells were generally seen in the platelet layer near the platelet-plasma interface. Visual analysis of the highlighted cells made in situ in the sample confirmed that they were malignant.

Figure 5:
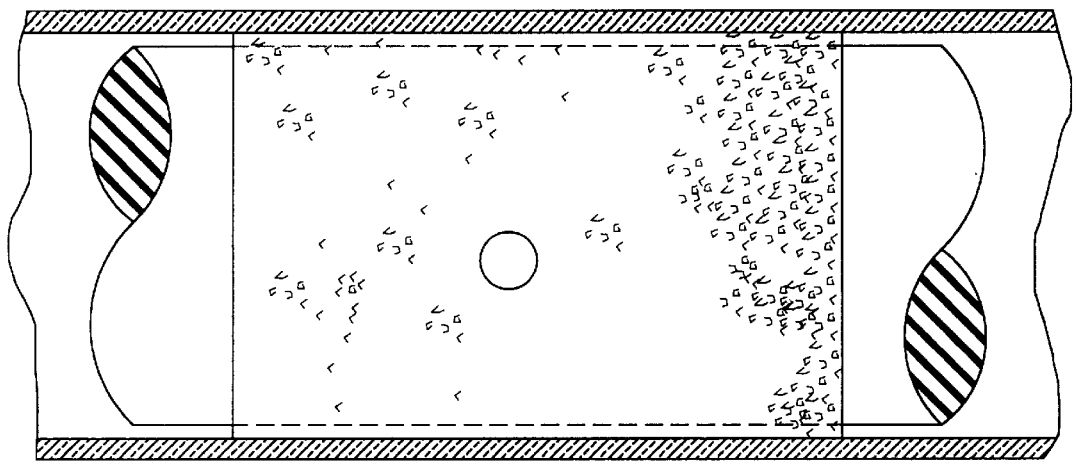
FIG. 5 is a graphic depiction of a photomicrograph taken of a single cultured HT-29 colon cancer cell added to a sample of acridine orange-stained anticoagulated whole blood using a 50x objective lens immersed in oil in an appropriately configured microscope assembly, which cell was isolated, visually identified, and visually confirmed in situ in the tube containing the centrifuged blood sample.

FIG. 5 is a recorded image of a single, rather large acridine orange-stained HT-29 colon cancer cell which was isolated in a 100 $\mu$l sample of blood that had been doped with a small concentration of cultured HT-29 cancer cells. The bright layer to the right of the cancer cell is an interface of the centrifuged platelet layer in the blood sample. This image was recorded at 500× magnification. Visual analysis of the highlighted cells made in situ in the sample confirmed that they were malignant.

Figure 6:
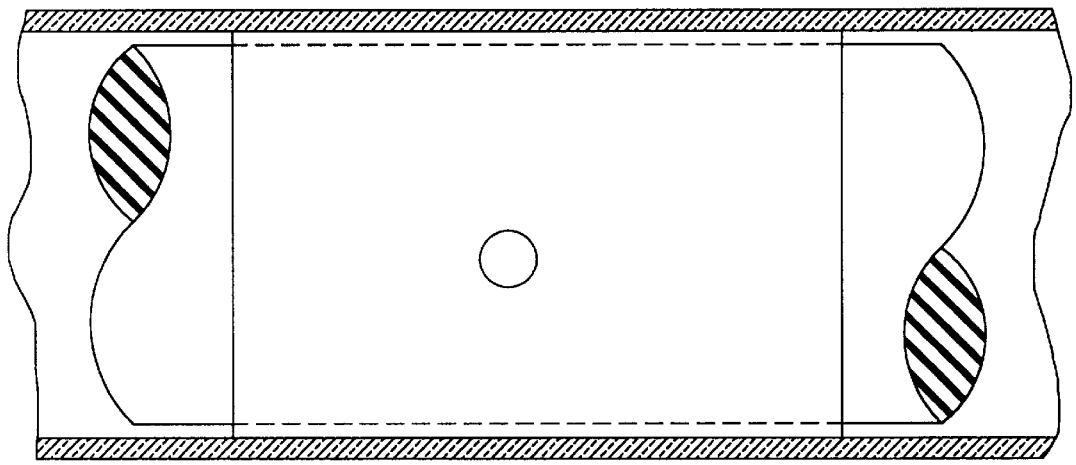
FIG. 6 is a graphic depiction similar to FIG. 5 of the photomicrograph taken in situ in a sampling tube of the single cultured HT-29 colon cancer cell in a sample of acridine orange-stained anticoagulated whole blood using a 50x objective lens immersed in oil in an appropriately configured microscopical instrument assembly, wherein the cancer cell was highlighted by Cy3-labeled E-cadherin in the centrifuged blood sample.

FIG. 6 is a view similar to FIG. 5, but showing the isolated HT-29 colon cancer cell as it appears when viewed through the E-cadherin/Cy3 filter set. It will be noted that all other cells in the field are not highlighted, while the HT-29 colon cancer cell is clearly visible, thus confirming the fact that the large cell is an epithelial cell. Visual analysis of the highlighted cell made in situ in the sample confirmed that it was malignant.

Figure 7:
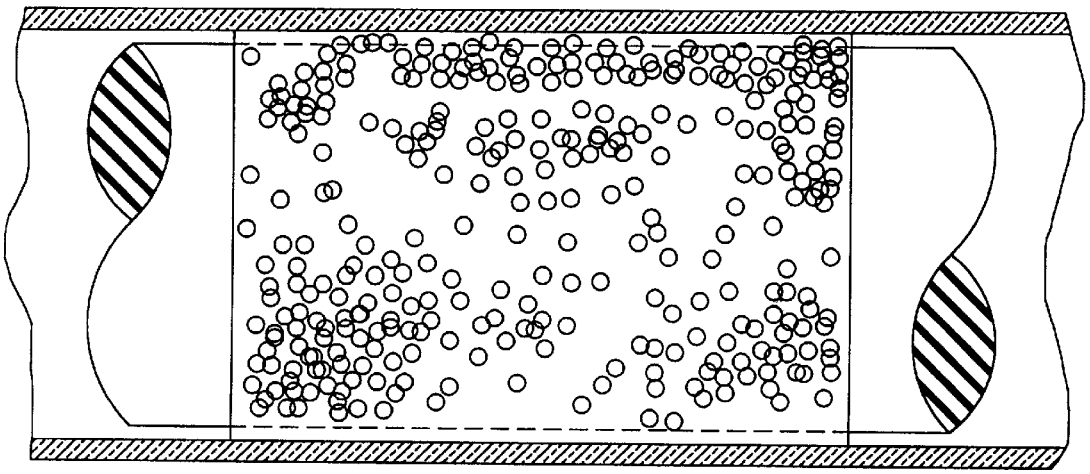
FIG. 7 is a graphic depiction of a photomicrograph taken in situ in a sampling tube of cultured HT-29 colon cancer cells which were added to a sample of acridine orange-stained anticoagulated whole blood and which were isolated, visually detected and confirmed using a 200x objective lens immersed in oil in an appropriately configured microscopical instrument assembly.

FIG. 7 illustrates the recorded images of acridine orange-stained cultured HT-29 colon cancer cells taken at 200× magnification, when larger populations of the cultured cancer cells were added to the blood sample. With the larger population of colon cancer cells, the cancer cells were seen to be distributed more widely throughout the platelet layer and were concentrated in several locations, one at the lymphocyte-platelet interface, and another at the platelet-plasma interface. Visual analysis of the highlighted cells made in situ in the sample confirmed that they were malignant.

Figure 8:
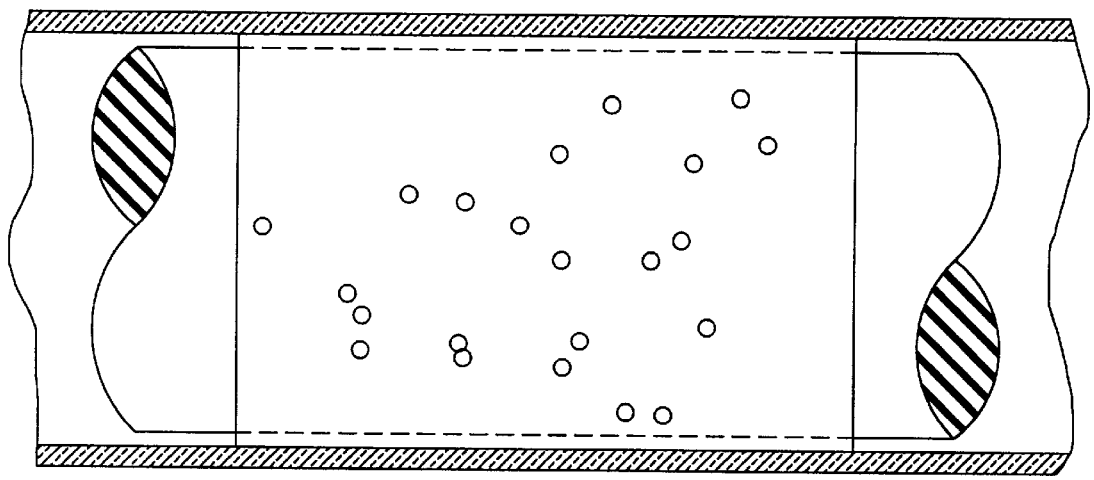
FIG. 8 is a graphic depiction similar to FIG. 7 of the photomicrograph taken of the cultured HT-29 colon cancer cells which were added to a sample of acridine orange-stained anticoagulated whole blood and which were isolated, visually detected and confirmed using a 200x objective lens immersed in oil in an appropriately configured microscopical instrument assembly, wherein the cancer cells were highlighted by Cy3-labeled E-cadherin in the centrifuged blood sample.

FIG. 8 is a view similar to FIG. 7 but showing the recorded images of E-cadherin/Cy3 stained colon cancer cells which confirms the epithelial origin of the highlighted cells. Visual analysis of the highlighted cells made in situ in the sample confirmed that they were malignant.

Figure 9:
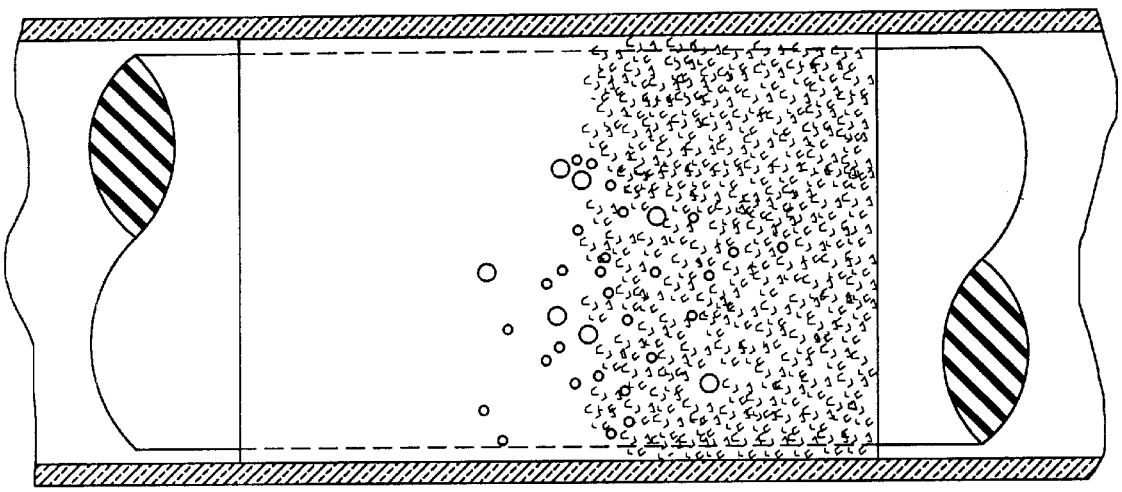
FIG. 9 is a graphic depiction of a photomicrograph taken of cultured HT-29 colon cancer cells which were added to a sample of acridine orange-stained anticoagulated whole blood and which were isolated, visually identified at 200x magnification, and visually confirmed in the centrifuged blood sample.
Figure 10:
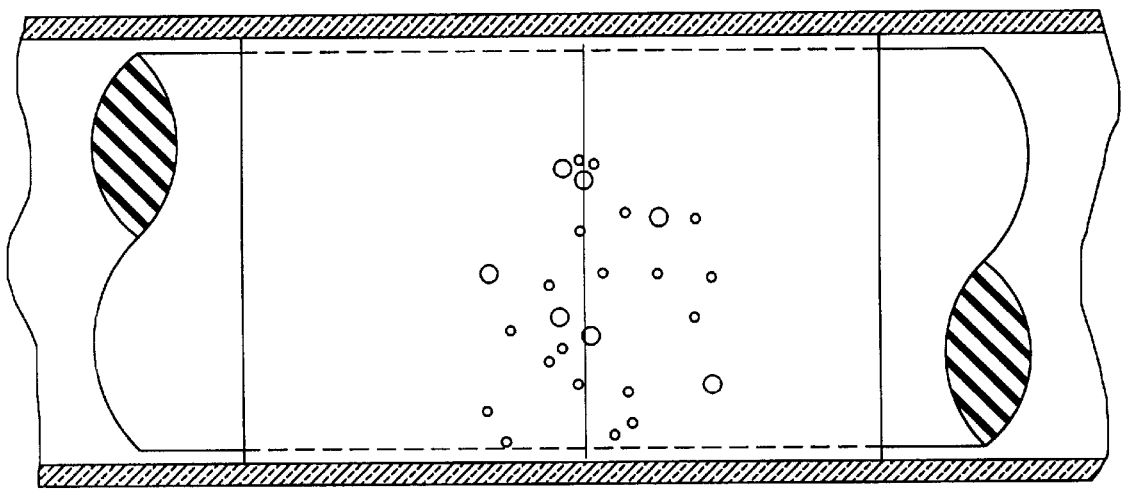
FIG. 10 is a graphic depiction similar to FIG. 9 of the photomicrograph taken of cultured HT-29 colon cancer cells in the sample of acridine orange-stained anticoagulated whole blood at 200x magnification wherein the cancer cells were highlighted by Cy3-labeled E-cadherin in the centrifuged blood sample.

FIGS. 9 and 10 are illustrative of recorded images of acridine orange-stained cultured HT-29 colon cancer cells which were added to a blood sample, and which were taken at 500× magnification. The cancer cells were seen to be concentrated near the platelet-plasma interface. FIG. 9 shows the cancer cells morphologically highlighted by acridine orange; and FIG. 10 shows the cancer cells epitopically highlighted by E-cadherin/Cy3. Thus FIG. 9 confirms the presence of nucleated cells in the plasma layer adjacent to the platelet layer of the centrifuged blood sample; and FIG. 10 confirms that certain ones of the detected nucleated cells are epithelial cells. Visual analysis of the highlighted cells made in situ in the sample confirmed that they were malignant.

Figure 11:
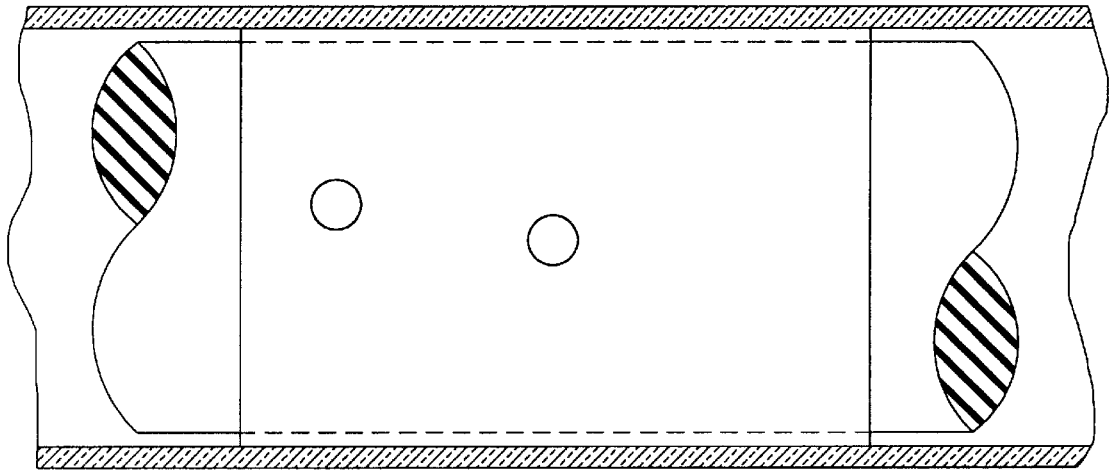
FIG. 11 is a graphic depiction of a photomicrograph taken of circulating breast cancer cells detected in a sample of acridine orange-stained anticoagulated whole blood taken from a patient known to have metastatic breast cancer, which cells were isolated, visually identified using a microscope assembly having a 50x objective lens, and visually confirmed in situ in the tube containing the centrifuged blood sample.
Figure 12:
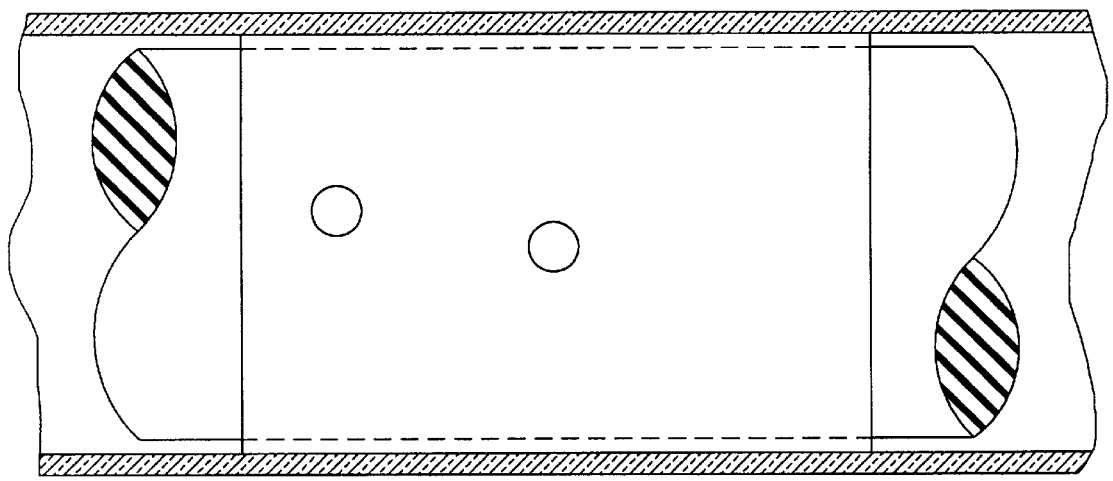
FIG. 12 is a graphic depiction similar to FIG. 11, but showing the circulating breast cancer cells highlighted by Cy3-labeled E-cadherin in the centrifuged blood sample.

FIGS. 11 and 12 are illustrative of recorded images of acridine orange-stained circulating breast cancer cells in a blood sample taken from a patient known to be suffering from metastatic breast cancer. The cancer cells were seen to be concentrated near the platelet-plasma interface. FIG. 11 shows the cancer cells morphologically highlighted by acridine orange; and FIG. 12 shows the cancer cells epitopically highlighted by E-cadherin/Cy3. Thus FIG. 11 confirms the presence of nucleated cells in the plasma layer adjacent to the platelet layer of the centrifuged blood sample; and FIG. 12 confirms that certain ones of the detected nucleated cells are epithelial cells. Visual analysis of the highlighted cells made in situ in the sample confirmed that they were malignant.

Figure 13:
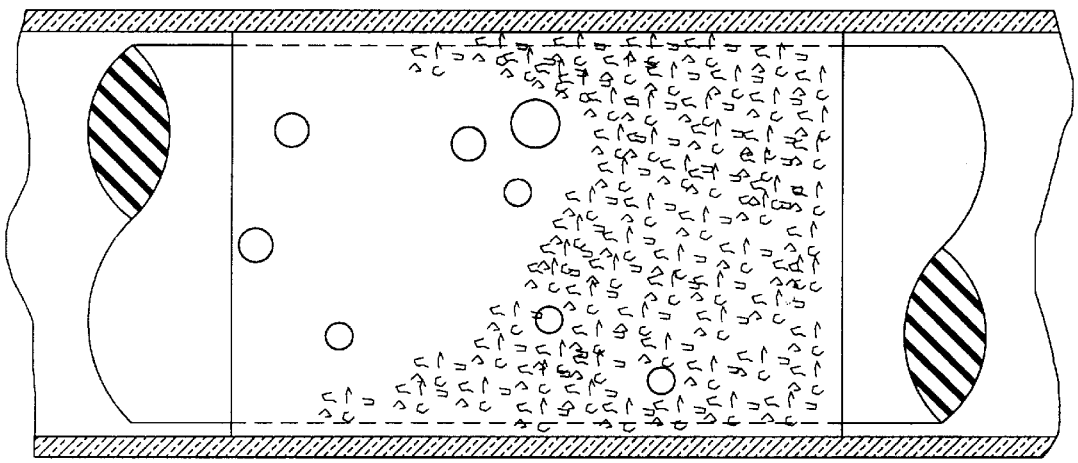
FIG. 13 is a graphic depiction of a photomicrograph taken of circulating prostate cancer cells taken from a patient known to have metastatic prostate cancer, and which cells were isolated, visually identified at 500x magnification, and visually confirmed in situ in the tube containing the centrifuged blood sample.
Figure 14:
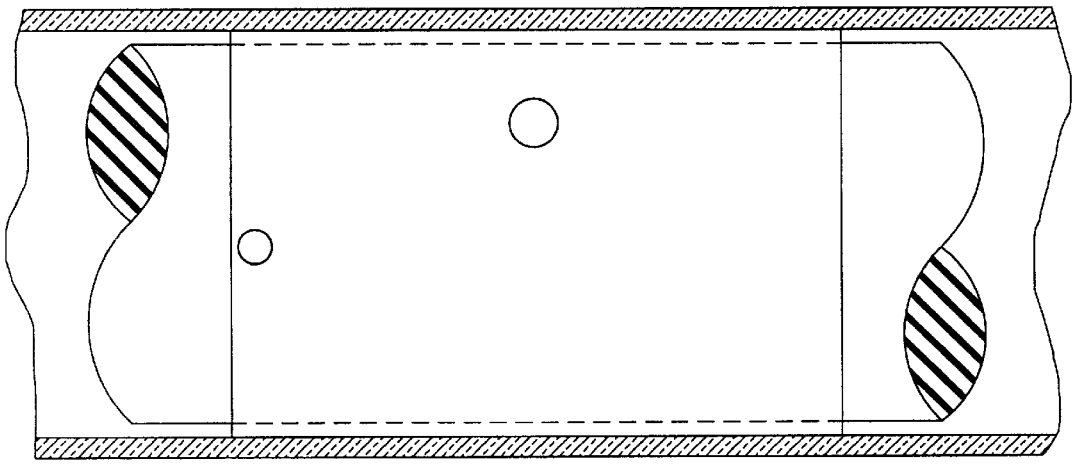
FIG. 14 is a graphic depiction similar to FIG. 13, but showing the circulating prostate cancer cells highlighted by Cy3-labeled E-cadherin in the centrifuged blood sample.

FIGS. 13 and 14 are illustrative of recorded images of acridine orange-stained circulating prostate cancer cells in a blood sample taken from a patient known to be suffering from prostate cancer. The cancer cells were seen to be concentrated near the platelet-plasma interface. FIG. 13 shows the cancer cells morphologically highlighted by acridine orange; and FIG. 14 shows the cancer cells epitopically highlighted by E-cadherin/Cy3. Thus, FIG. 13 confirms the presence of nucleated cells in the plasma layer adjacent to the platelet layer of the centrifuged blood sample; and FIG. 14 confirms that certain ones of the detected nucleated cells are epithelial cells. Visual analysis of the highlighted cells made in situ in the sample confirmed that they were malignant. The fact that not all cells are highlighted by Cy3 markers provides an internal negative control which confirms that the epitopically highlighted cells are epithelial in origin. Non-epitopically highlighted nucleated cells are lymphocytes.

Experiments were also conducted to determine the sensitivity of the aforesaid assay. The standard "QBC" capillary tube holds 100 $\mu$l of blood which contains $1\times10^9$ of red blood cells (RBCs) and $1\times10^6$ of nucleated cells (granulocytes, lymphocytes, etc.). Thus, without changing the scale of the test, the theoretical limit of sensitivity would be 1 cell in $1\times10^6$ of nucleated cells. Serial dilutions of HT-29 colon cancer cells were used to obtain multiple paired 10 $\mu$l aliquots containing between 1 and 10 cells, or pairs containing between 10 and 100 cells. The first aliquot of the pair was added to the "QBC" tubes and the second was counted with a standard hemocytometer. These experiments led to the conclusion that the limit of sensitivity of this assay approaches the theoretical limit of 1 cell in $1\times10^6$ of nucleated cells using a 110 $\mu$l tube. Theoretically the sensitivity of the test can be increased up to ten fold by performing the analysis in a 1 ml blood sampling tube.

Although morphometric analysis may be sufficient for identification of cancer cells, other methods of verification may also be necessary. The assay of this invention takes advantage of the fact that it can detect abnormal cell morphology, and can also, at the same time, verify the epithelial or hematologic progenitor origin of any abnormal nucleated cells noted in the blood sample. Since the analysis of this invention is non-destructive of the cells, the cells may be removed from the sampling tube for additional analysis by other methods such as the PCR method described in the prior art, or by biochemical assay.

As an example we chose E-cadherin since this antigen is highly specific for epithelial cells and is displayed on the external surface of the cell membrane. For these studies we used Cy3, which is a cyanamine-based fluorophore, and which was conjugated directly to E-cadherin monoclonal antibodies to be able to visualize cell staining at a wavelength other than that used for morphometric examination using acridine orange-induced fluorescence.

We have confirmed that malignant nucleated epithelial cells can be morphometrically identified in a centrifuged sample of anticoagulated whole blood using the technique of this invention. Suitable morphometric criteria which can be visualized in the blood sample in situ in the tube assembly include: intracellular nuclear/cytoplasmic ratios; intracellular nuclear size and shape; intracellular nuclear chromatin pattern; the thickness and size of the nuclear membrane; and the number and size of nucleoli; among other things. We have also determined that epithelial cancer cells and hematologic progenitor cells layer out in the centrifuged anticoagulated whole blood sample by density, rather than by sedimenting out in the blood sample by size. This determination allows the detection of circulating cancer cells and/or hematologic progenitor cells in a predetermined and known zone in the centrifuged blood sample, i.e., in the zone of the centrifuged blood sample where the platelets layer out. If the circulating cancer and/or hematologic progenitor cells were to sediment out in the blood sample by size, one would be unable to define an "zone of interest" where the cancer and/or hematologic progenitor cells would be expected to be found. The cancer and/or hematologic progenitor cells have been found predominantly near the platelet/plasma interface; within the platelet layer near the lymphocyte/platelet interface; or in the lymphocyte layer in artificially overloaded cases, all depending upon the concentration of cancer and/or hematologic progenitor cells which are in the blood sample. A theoretical sensitivity of the technique of this invention, when employing a 100 $\mu$l capillary tube containing $1\times10^6$ nucleated cells, is one detected cancer and/or hematologic progenitor cell in $1\times10^6$ nucleated blood cells in a 100 $\mu$l blood sample is attainable. As noted above, a ten fold increase in the theoretical sensitivity should be achievable if the volume of the blood sample were increased ten fold, to about one milliliter. Verification of the origin of cancer and/or hematologic progenitor cells in the blood sample can be confirmed by immunofluorescent labeling of suspicious cells. Thus visual inspection of the cells will determine whether they display cancerous morphometric characteristics, and immunofluorescence will verify the origin of the suspicious cells being inspected.

It will be appreciated that the aforesaid procedures and apparatus can be used to screen patients for the presence or absence of cancer cells; can be used to assess staging of a malignant tumor; can be used to assess the effectiveness of chemotherapy on patients being treated for cancer; and can be used to identify and enumerate hematologic progenitor cells in the blood sample. The detection and enumeration of hematologic progenitor cells and cancer cells is of clinical importance for stem cell harvesting and purging of cancer cells from harvested stem cells. The use of this invention as a means to assess the effectiveness of chemotherapy provides a much more sensitive and rapid way to evaluate the therapy than does CAT scanning, X-ray, or the like which are presently used to monitor the size of a tumor. The effectiveness of chemotherapy may be assessed by counting the number of cancer cells in the blood sample. The counting procedure can be performed throughout the entire periphery of the well-defined zone of the tube, or it can be performed throughout only a portion of the periphery of the aforesaid zone of the tube. When the latter approach is taken, the number of cancer cells in the sample can be extrapolated by solving the formula:

$$C = N(360°/d) \div V;$$

wherein "C" is the resultant cell concentration; "N" is the number of target cells counted; "d" is the degree of rotation of the tube which was examined for target cells divided by "V" which is the volume of the sampling tube. The cell enumerating can be performed by means of a photometric counter, or can be done visually. The photometric approach can use a combination of epitopic labels which will differentially highlight either cancer and/or hematologic progenitor cells or other non-cancer cells. In this manner the highlighted and/or non-highlighted cells will be counted. The morphometric analysis can also be performed photometrically. The visual approach can use a morphometric stain such as acridine orange or the other morphometric stains identified above.

Advantages of the "QBC" technique and apparatus to diagnose and enumerate cancer cells in circulating blood over the FACS and molecular techniques include: 1) the relatively short period of time needed to perform the blood analysis; 2) the fact that the system can be integrated into standard laboratory equipment that all pathologists are capable of using without extensive training; 3) unfixed cells can be examined in a fluid medium so as to eliminate fixation artifacts; 4) only a relatively small blood volume is needed to perform the analysis; 5) the technique is equally sensitive as the molecular technique in that one cancer cell can be detected in a sample containing $10^6$–$10^7$ normal nucleated cells; 6) the fact that the "QBC" technique utilizes a closed sampling and analysis system so as to eliminate cross contamination, which is a major problem in the molecular procedure; 7) the elimination of cellular contamination due to contaminating floating cells in fixation stains which are used in routine cytological procedures; and 8) the analysis of this invention is safer for the technicians performing the analysis since they will not be exposed to the blood sample being analyzed.

The specific insert and tube shown in the drawings are cylindrical; however, they could also be made polygonal. The only limiting factor regarding the transverse configurations of the tube and insert is that they be complimentary with each other. The analysis of the blood sample is made under suitable magnification by a microscopical instrument, preferably equipped with a CCD camera. The gap formed in the tube between the tube and the insert is transversely sized so that individual target cells can be isolated and can be readily discerned, enumerated and morphometrically analyzed within the gap. The transverse thickness of the gap is also within the focal operating range of the microscopical instrument being used to analyze the gap. The transverse thickness of the gap is in the range of about 10 microns to about 100 microns.

It will be appreciated that the method of this invention, in its broadest sense, involves detecting the presence or absence of individual circulating target nucleated cells in a centrifuged sample of anticoagulated whole blood contained in a tube that also contains a generally cylindrical insert. The insert forms a well-defined annular zone in the tube. The blood sample is combined with one or more epitope-specific labeling agents that are operative to produce a characteristic signal result on target nucleated cells, which result can include no signal at all, and which result defines the presence or absence of one or more epitopes on the target nucleated cells. The blood sample is also combined with a colorant which is operable to clarify cell morphology in all nucleated cells in the blood sample. Circulating nucleated cells are thus identified by cell morphology, and all identified nucleated cells which by reason of their morphology may be target cells are further characterized as target or non-target cells epitopically. By way of further explanation, assume that a specific combination of epitopes "A" and "B" is characteristic of a target cell, but not characteristic of other cells in the blood sample. The presence or absence of only one of these epitopes; or the presence or absence of both of these epitopes could be characteristic of the target cell. Thus, any one of four different respective epitope-specific labeling agent signal results of: A and no B; B and no A; both A and B; or no A and no B, could be used to characterize the target cell. The identifying and characterizing steps can be performed in situ in the tube. Obviously, more, or less, than two different epitopes could be employed in the characterization of target cells.

Since many changes and variations of the disclosed embodiment of the invention may be made without departing from the inventive concept, it is not intended to limit the invention otherwise than as required by the appended claims.

What is claimed is:

1. A method for detecting the presence or absence of individual circulating epithelial cancer cells in an anticoagulated whole blood sample, said method comprising the steps of:
    a) providing a transparent container having a cavity containing an insert, said container and insert combining to form a free volume between the insert and the walls of the container;
    b) combining the blood sample with one or more epitope-specific labeling agents so as to differentiate any individual epithelial cancer cells from other cells in the blood sample;
    c) combining the blood sample with a colorant which is operable to clarify individual epithelial cancer cell morphology in all individual epithelial cancer cells in the blood sample;
    d) placing the blood sample in the container and centrifuging the blood sample in the container so as to cause any individual epithelial cancer cells present in the blood sample to localize in said free volume in the container;
    e) enumerating any individual differentiated epithelial cancer cells found in situ in the free volume in the container;
    f) examining the cell morphology of any individual differentiated epithelial cancer cells in situ in the free volume in the container;
    g) said combining steps being performed either before or after the blood sample is placed in the container; and
    h) said enumerating and examining steps being performed in no particular order.

2. A method for detecting the presence or absence of cancerous cell morphology in individual circulating epithelial cells in a centrifuged sample of anticoagulated whole blood contained in a container which container also contains an insert which forms a free volume in the container, said blood sample having been combined with one or more labeling agents that are specific to one or more epitopes on the epithelial cells, and said blood sample having also been combined with a colorant which is operable to clarify epithelial cell morphology in individual epithelial cells in the blood sample, said method comprising the steps of identifying a percentage of all individual labeled epithelial cells which are disposed in said free volume in situ in the container, and examining the cell morphology of any such individual identified epithelial cells in situ in the container so as to determine whether any such individual identified epithelial cells display cancerous cell morphology.

3. A method for identifying individual circulating cancerous epithelial cells in a centrifuged sample of anticoagulated whole blood which sample is contained in a transparent container, which container also contains an insert, and which blood sample has been combined with at least one labeling agent that is specific to at least one epithelial cell epitope, and which blood sample has also been combined with a colorant that clarifies nucleated cell morphology, said method comprising the steps of examining a free volume located between the insert and the container wall wherein buffy coat constituents in the blood sample gravitate during centrifugation and enumerating any individual labeled epithelial cells having cancerous morphology in situ in the container, which individual labeled epithelial cells have localized during centrifugation in said free volume in the container.

4. A method for differentiating individual cancer cells from individual hematologic progenitor cells and from other nucleated cells in a sample of anticoagulated whole blood, said method comprising the steps of:
   a) providing a sample of anticoagulated whole blood containing epitopic cell labeling materials which are operable to differentiate cancer cells and hematologic progenitor cells from each other and from other nucleated cells in the sample, said sample being contained in a transparent container which also contains an insert that is operable to form a well-defined free volume in the container;
   b) centrifuging the sample of blood in the container so as to gravimetrically separate the blood sample into its formed constituent components and so as to cause any nucleated cells which are not conventional blood cells in the sample to localize in said well-defined free volume in the container; and
   c) examining said well-defined free volume in the container in order to determine whether any cancer or hematologic progenitor cells are present in said well-defined free volume in the container.

5. A method for detecting individual cancer cells and/or individual hematologic progenitor cells in a sample of anticoagulated whole blood, said method comprising the steps of:
   a) providing a sample of anticoagulated whole blood containing cell epitope labeling materials which are operable to differentiate cancer cells and/or hematologic progenitor cells from other nucleated cells in the sample, said sample being contained in a transparent container which also contains an insert that is operable to form a well-defined free volume in the container;
   b) centrifuging the sample of blood in the container so as to gravimetrically separate the blood sample into its constituent formed components and so as to localize any nucleated cells in the sample in said well-defined free volume in the container;
   c) examining said well-defined free volume in the container in order to determine whether any epitopically differentiated nucleated cells are present in said well-defined free volume in the container; and
   d) enumerating any individual cancer cells and/or individual hematologic progenitor cells which are found to be present in said well-defined free volume in the container.

6. A method for analyzing a sample of anticoagulated whole blood in order to determine the presence or absence of individual cancer cells in the sample, said method comprising the steps of:
   a) providing a sample of anticoagulated whole blood containing cell epitope-labeling materials which are operable to differentiate cancer cells from other nucleated cells in the sample, said sample being contained in a transparent container which also contains an insert that is operable to form a well-defined free volume in the container;
   b) centrifuging the sample of blood in the container so as to gravimetrically separate the blood sample into its constituent formed components and so as to deposit individual cancer cells in the sample, in said well-defined free volume in the container; and
   c) examining said well-defined free volume in the container in order to determine whether any individual differentiated cancer cells are present in said well-defined free volume in the container.

7. A method of identifying individual circulating epithelial cancer cells in a centrifuged sample of anticoagulated whole blood which sample is contained in a transparent container, which container also contains an insert that forms a well defined free volume in the container, and which blood sample has been combined with at least one labeling agent that is specific to at least one epithelial cancer cell epitope, said method comprising the steps of examining said well-defined free volume in the container wherein white cells and platelets in the blood sample have gravitated during centrifugation; and identifying any individual labeled epithelial cancer cells in situ in the container which labeled cells have localized in said well-defined free volume in the container during centrifugation of the sample in the container.

8. A method for detecting the presence or absence of individual circulating nucleated epithelial cells in an anticoagulated whole blood sample, said method comprising the steps of:
   a) providing a transparent container having a bore containing an insert, said container and insert combining to form a well-defined free volume in the container bore;
   b) combining the blood sample with one or more epitope-specific labeling agents so as to differentially highlight individual nucleated epithelial cells which may be present in the blood sample;
   c) combining the blood sample with a colorant which is operable to clarify cell morphology in individual nucleated cells in the blood sample;
   d) placing the blood sample in the container and centrifuging the blood sample in the container so as to cause individual nucleated epithelial cells present in the blood sample to gather in said well-defined free volume in the container bore;
   e) enumerating individual labeled epithelial cells found in situ in the well-defined free volume in the container bore;

f) examining the cell morphology of any individual labeled cells in situ in the well-defined free volume in the container;

g) said combining steps being performed either before or after the blood sample is placed in the container; and h) said enumerating and examining steps being performed in no particular order.

9. The method of claim 8 wherein said enumerating and examining steps are performed with an automated microscope-like instrument.

10. The method of claim 9 wherein said well-defined free volume has a transverse thickness which is essentially equal to a focal operating range of the microscope-like instrument at a predetermined power.

11. The method of claim 10 wherein said transverse thickness is within a range of about ten to about one hundred microns.

12. A method for detecting the presence or absence of individual circulating hematologic progenitor nucleated cells in an anticoagulated whole blood sample, said method comprising the steps of:

a) providing a transparent container having a bore which contains an insert, said container and insert combining to form a well-defined free volume between said insert and a wall of said container bore which well-defined free volume has a transverse thickness that is at least about ten microns;

b) combining the blood sample with one or more labeling agents which are specific to surface receptors on hematologic progenitor cells so as to differentiate any individual hematologic progenitor cells from other formed components in the blood sample;

c) combining the blood sample with a colorant which is operable to clarify cell morphology in all nucleated cells in the blood sample;

d) placing the blood sample in the container and centrifuging the blood sample in the container so as to cause individual hematologic progenitor cells present in the blood sample to gather in said well-defined free volume in the container;

e) examining the well-defined free volume under magnification and enumerating individual differentiated hematologic progenitor cells found in situ in the well-defined free volume in the container;

f) examining under magnification the cell morphology of individual differentiated cells in situ in the well-defined free volume in the container;

g) said combining steps being performed either before or after the blood sample is placed in the container; and h) said enumerating and examining steps being performed in no particular order.

13. A method for detecting the presence or absence of individual circulating cancer cells in a centrifuged sample of anticoagulated whole blood contained in a container which container also contains an insert that forms a well-defined free volume in the container, said blood sample having been combined with one or more epitope-specific labeling agents that are operative to produce a characteristic signal result on individual cancer cells, and which result is defined by the presence of one or more epitopes on the individual cancer cells, and said blood sample having also been combined with a colorant which is operable to clarify cell morphology in all nucleated cells in the blood sample, said method comprising the steps of identifying by cell morphology all nucleated cells disposed in said well-defined annular free volume, and further characterizing all identified individual nucleated cells as cancer cells or non-cancer cells epitopically, said identifying and characterizing steps being performed in situ in the container.

* * * * *